United States Patent [19]

Hagarty

[11] Patent Number: 5,116,618

[45] Date of Patent: May 26, 1992

[54] WATER-SOLUBLE ARTHROPODICIDALLY-ACTIVE FOAM MATRIX AND METHOD OF MANUFACTURE

[75] Inventor: John D. Hagarty, Racine, Wis.

[73] Assignee: S. C. Johnson & Son, Inc., Racine, Wis.

[21] Appl. No.: 569,499

[22] Filed: Aug. 20, 1990

Related U.S. Application Data

[63] Continuation of Ser. No. 339,565, Apr. 17, 1989, abandoned, which is a continuation-in-part of Ser. No. 922,926, Oct. 24, 1986, Pat. No. 4,889,710, which is a continuation of Ser. No. 727,932, Apr. 26, 1985, abandoned.

[51] Int. Cl.⁵ .............................................. A01N 25/16
[52] U.S. Cl. ................................. 424/405; 424/43; 424/45; 424/409
[58] Field of Search ................. 424/405, 409, 43, 45

[56] References Cited

U.S. PATENT DOCUMENTS

| | | |
|---|---|---|
| 2,754,243 | 7/1956 | Gysla et al. |
| 2,903,478 | 9/1959 | Lambrech |
| 3,042,703 | 7/1962 | Schegk |
| 3,076,744 | 2/1963 | Geary |
| 3,111,539 | 11/1963 | Böcker |
| 3,303,091 | 2/1967 | Mailander ........................ 424/45 |
| 3,524,911 | 8/1970 | Leavitt |
| 3,716,600 | 2/1973 | Magee |
| 3,736,338 | 5/1973 | Gates et al. |
| 3,791,983 | 2/1974 | Maierson |
| 3,816,610 | 6/1974 | Lusby |
| 3,818,047 | 6/1974 | Henrick |
| 3,833,635 | 9/1974 | Henrick |
| 3,845,172 | 10/1974 | Magee |
| 3,865,874 | 2/1975 | Henrick |
| 3,970,584 | 7/1976 | Hart et al. |
| 4,286,020 | 8/1981 | Himel et al. |
| 4,439,342 | 3/1984 | Albanese ........................ 424/43 |

FOREIGN PATENT DOCUMENTS

| | | |
|---|---|---|
| 596091 | 10/1950 | Belgium |
| 594669 | 9/1959 | Belgium |
| 1116656 | 5/1958 | Fed. Rep. of Germany |
| 2538470 | 8/1978 | Fed. Rep. of Germany |
| 45-11719 | 4/1970 | Japan ........................ 424/45 |
| 48-10205 | 4/1973 | Japan ........................ 424/45 |
| 48-10536 | 4/1973 | Japan ........................ 424/45 |
| 54-23123 | 2/1979 | Japan ........................ 424/45 |
| 5764601 | 10/1980 | Japan |
| 8501876 | 5/1985 | PCT Int'l Appl. ............... 424/43 |
| 1107140 | 10/1965 | United Kingdom |

Primary Examiner—Lester L. Lee

[57] ABSTRACT

A novel arthropodicidally-active composition-of-matter is disclosed. Such comprises an aqueous lower alkanol solvent, a toxicant contained within the solvent, and an effective amount of an emulsifier, also contained within the solvent, for forming a foam matrix of predetermined stability. Also disclosed are methods for producing such a composition-of-matter.

4 Claims, No Drawings

WATER-SOLUBLE ARTHROPODICIDALLY-ACTIVE FOAM MATRIX AND METHOD OF MANUFACTURE

REFERENCE TO RELATED APPLICATIONS

This new patent application is a Ser. No. 07/339,565, filed Apr. 17, 1989 (now abandoned) which is a continuation-in-part of U.S. application Ser. No. 922,926 (now U.S. Pat. No. 4,889,710) filed Oct. 24, 1986, which, in turn, is a continuation of my earlier U.S. application Ser. No. 727,932 filed Apr. 26, 1985 (now abandoned), the benefit of which is now claimed for purposes of priority pursuant to 35 USC § 120.

TECHNICAL FIELD OF THE INVENTION

My present invention si generally directed to an arthropodicidally-active composition-of-matter and to its method of manufacture. My novel composition-of-matter is generally characterized as a stable foam matrix. Still more particularly, my novel arthropodicidally-active stable foam matrix is water-soluble.

For purposes of my present invention, I shall use the term "arthropod", which is generally under by those skilled in the art of "pest" control as connoting any member of a large group of invertebrate animals with joined legs and segmented bodies. In particular, I shall use the entomologically-known term "arthropod" in its "generic" sense so as to include arachnids, crustaceans, insects and myriapods.

BACKGROUND OF THE INVENTION

One's home is one's castle; and most people do not wish to share their castles with tiny, crawling pests such as ants, centipedes, pill bugs or spiders. Indeed, ridding one's home of small, crawling pests of these and other sorts can at times become a matter of concern, and effectively (i.e. totally) ridding one's home of such pests can thus pose a problem. Furthermore, with regard to any pesticide that is to be used in the home, the pesticidal activity as well as the physical appearance (of such a pesticidal composition) often plays an important role in a decision by today's consumer as to whether to purchase one particular pesticidally-effective product instead of another.

The amount of money spent annular on insect control by consumers is moreover sizable and well known; and, there is a noticeable on-going quest for better, ever more effective pesticides. Indeed, a variety of prior-art pesticidal compositions are well known.

For example, U.S. Pat. No. 3,816,610 to Lusby discloses a so-called "palatable", foamed rodent-control material. Such a rodent-control material, more particularly, is said to comprise a rodent control agent such as a rodenticide which, in turn, a interspersed throughout a so-called "plastic foam cellular" structure. The foal cellular structure is produced by combining isocyanate with a mixture consisting of a polyol, a catalyst, a blowing agent, and a so-called "rodent-control" agent. Lusby discloses that such ingredients, after being thus combined, react chemically and expand in volume up to fifty (50) or more times, via so-called "foaming action". Lusby further discloses that the result of such a volume expansion is the production of a low-density substance or mass (i.e., a "foam"), which is said to be able to fill up cavities and taken their shape, wherein such a mass quickly becomes rigid.

U.S. Pat. No. 3,524,911 to Leavitt discloses an insecticidal composition. More particularly, Leavitt discloses that the insecticidal composition, which is preferably utilized as an aerosol sprayable composition, comprises a so-called "substantially non-aqueous" mixture, which is said to include a toxic concentration of a vaporizable insecticide as well as a so-called "substantially inert" foam-forming carrier. After this insecticidal composition is dispensed from its aerosol spray container, the foam-forming carrier is aid to form a so-called "stable" (i.e. a form-sustaining) foam. Leavitt further discloses that the insecticide is released from such a foam carrier in toxic concentrations at a controlled rate over a prolonged period of time.

U.S. Pat. No. 3,970,584 to Hart et al. discloses a personal-care foam-forming emulsion that is utilized to produce a rich, creamy, shiny foam having a so-called "fine" or "delicate bubble" structure. Hart et al. teach that such a foam can be utilized to produce a variety of personal-care types of products. In particular, Hart et al. specifically teach that such a rich, creamy, shiny foam can be utilized to produce an insect-repellent personal-care type of product. Hart et al. further specifically teach that their personal-care type of foam products can have certain unique characteristics which, in turn, are said to be particularly desirable in the personal-care field. In particular, Hart et al. point out that their foam product will have a so-called "fine" or "delicate" bubble structure, and that such a foam product will, as a result, possess desirable foam-density and foam-stiffness personal-care types of qualities.

German Pat. ("Offenlegungsschrift") No. 25 38 470 discloses a method for producing a pesticidally-active composition-of-matter, characterized as an attractant in admixture with a toxicant, wherein the composition-of-matter is produced by a method whereby the attractant and toxicant are absorbed into a piece of plastic foam by so-called "electrostatic" forces.

U.S. Pat. No. 3,076,744 to Geary discloses a particular insecticidal bait composition, which is said to include a so-called "polymerized aminoplast" and an insect-edible attractant in admixture with an organic insecticide. The attractant and the insecticide, in turn, are said to be "molecularly occluded" within the polymerized aminoplast. Geary further discloses that the polymerized aminoplast, containing the above-mentioned "occluded" ingredients, can be crushed to a fine-particle size and thereafter spread, for example, in insect-infested areas.

U.S. Pat. No. 3,791,983 to Maierson discloses certain sprayable and so-called "aerosolizable" web-forming compositions. Such compositions, in particular, are characterized as being self-supporting, three-dimensional webs of randomly-associated, joined monofilaments ranging in average diameter of from about 1 to 10 microns. Such so-called "web-forming" compositions of this sort are said to be utilizable for the purpose of encapsulating insecticidal ingredients. Insecticidal ingredients thus encapsulated can then be used to combat insects.

U.S. Pat. No. 4,286,020 to Himel et al. also discloses a process for the encapsulation of certain insecticidal particles.

British Pat. No. 1,107,140 to Mitchell et al. discloses an insecticidally-active oil-in-water emulsion which, after being dispensed from an aerosol-type dispenser, preferably is so formulated as to produce a spray rather than a foam.

In view of the many features and advantages of the above-discussed prior-art pesticidal products, as well as certain other prior-art pesticidal products (which are presently commercially available), present-day consumers nevertheless continue to seek ever novel pesticidal compositions-of-matter for a variety of reasons. For example, easy clean-up or disposal of a variety of now-inactive pesticidal products is desirable. Pesticidally-active compositions are of course known, in general, to posses a finite activity period. To facilitate clean-up of compositions rendered pesticidally-inactive due to the passage of time, it would be desirable that such a pesticidally-active composition be water-soluble.

Still further, for the manufacturer of such a product, it would be desirable that the ingredients be relatively low-cost; and it would be even more desirable that such a product be relatively inexpensive to manufacture as well.

SUMMARY OF THE INVENTION

Accordingly, I have discovered a relatively low-cost method of preparing a novel pesticidally-active composition-of-matter. The essential ingredients, moveover, are relatively low cost. My novel pesticidally-active composition-of-matter is characterized as a stable foam matrix. Depending upon the relative amounts as well as the specific types of ingredients that are utilized in the manufacture of the novel pesticidally-active composition-of-matter of my present invention, the foam matrix can so be formulated as to be substantially stable for hours or weeks (or even months), as desired. Still further, and as was briefly mentioned above, my novel composition-of-matter is water-soluble, a markedly desirable characteristic and/or quality (or feature), which enables easy clean-up and/or disposal of the composition, after it is rendered inactive due to the passage of time.

Furthermore, my novel pesticidally-active composition-of-matter is suitable for purposes of controlling a wide variety of arthropod pests. For example, and depending upon the relative amount and particular types of ingredients chosen, my novel composition-of-matter can specifically be so formulated as to be effective for controlling certain crustaceans (such as pill bugs), of certain arachnids (such as spiders), or a wide variety of well-known crawling insects (such as ants, cockroaches, crickets, earwigs, sewer flies, silverfish, and the like), or certain myriapods (such as millipedes and centipedes), or certain combinations of these classes, i.e. arachnids, crustaceans, insects and myriapods (within the phylum "arthropoda").

Still further, and in accordance with certain general principles and features of my present invention, my novel composition-of-matter can specifically be so formulated as to be effective for killing a wide variety of arthropod pests upon direct contact or upon ingestion (or both), as desired. In other words, certain specific formulations of my novel composition-of-matter are effective so-called "contact-type" arthropodicides, whereas certain other specific formulations of my novel composition-of-matter can be so formulated as to be arthropod-edible and will be effective arthropodicides upon ingestion.

My present invention is thus generally directed to an arthropodicidally-active composition-of-matter and to its method of manufacture. Such a composition-of-matter, briefly stated, comprises an aqueous lower alkanol solvent, and an emulsifier as well as a toxicant, each contained within the solvent. The amount of emulsifier, relative to the amount of solvent, is effective for purposes of forming a foam matrix of predetermined stability.

DETAILED DESCRIPTION OF THE PREFERRED EMBODIMENTS

While the present invention is susceptible to embodiment in various forms, there is hereinafter described in detail a variety of presently-preferred embodiments of my present invention. The detailed description presented hereinbelow is therefore to be considered as but an exemplification of my present invention without limitation to the specific embodiments disclosed and discussed.

As was briefly previously mentioned, my present invention is generally directed to an arthropodicidally-active composition-of-matter and to its method of manufacture. Such a composition-of-matter comprises an aqueous lower alkanol solvent such as a $C_1$ to $C_4$ alcohol solvent. The aqueous lower alkanol solvent is generally present in the composition-of-matter in an amount of about 3 to about 40 parts-by-weight lower alkanol, preferably about 4 to about 30 parts-by-weight lower alkanol, and more preferably about 5 to about 20 parts-by-weight lower alkanol, based upon one-hundred (100) parts-by-weight of total water and lower alkanol. A preferred lower alkanol is ethanol.

My arthropodicidally-active composition-of-matter further comprises an emulsifier as well as a toxicant, each contained within the aqueous lower alkanol solvent.

As an optional ingredient, my arthropodicidally-active composition-of-matter can further include an attractant.

Attractants suitable for purposes of inclusion in the composition-of-matter of my present invention are well-known in the art. Indeed, any particular material that is compatible with the stable foam matrix and specifically attractive to (and/or edible by) a particular arthropod that is to be targeted for extermination or control may be employed. Accordingly, when employed for use against a particular arthropod, any edible material that is known to be particularly attractive to such an arthropod can of course be selected.

For sweet-loving ants and other sweet-loving insects such as cockroaches, for example, the edible attractant can be sucrose, fructose, glucose, maltose, honey, molasses, brown sugar, maple sugar, fruit syrup, corn syrup, maple syrup, or beet syrup, as well as ground raisins and other ground sweet fruits. In particular, a corn sweetener that is presently commercially available under the "Corn Sweet 90" brand name and which includes about ninety (90) weight-parts corn-derived fructose, has been found to be particularly suitable in controlling cockroaches.

Other types of insects may prefer particles of certain cereals, particles of certain brans or particles of certain meals of various origin. Still other types of insects such as fire ants are known to prefer certain animal and/or certain vegetable oils and fats containing (or combined with) certain proteins.

As still further examples of such edible materials, there may be mentioned beef fat, bacon, fish meals, eggs, meals and extracts (such as vanilla extract), port sausage, tankage (50% protein, meat and bone scraps), dried brewer's solubles, cottonseed, soybean, corn, coconut, olive, palm, and poppyseed, nuts, vegetable oils (such as soybean oil), fats, meals, extracts and the like, of predetermined particle size, as well as butter, bacon drippings, lard, vegetable protein extracts and hydrolyzates, and tallow, as well as mixtures of these various attractants.

Such an attractant, which is (as was mentioned above) optional, may be employed in the arthropodicidally-active composition-of-matter in any desired proportion, generally ranging from about 0.5 to about 20 parts-by-weight, and preferably ranging from about 3 to about 12 parts-by-weight, per one-hundred (100) parts-by-weight of the arthropodicidally-active composition-of-matter.

Toxicants suitable for purposes of inclusion in the composition-of-matter of my present invention are well-known in the art. Moreover, the stable foam matrix of my present invention can include a toxicant having a delayed effect (which is useful in controlling social insects such as ants), or the stable foam matrix can include a toxicant having an immediate effect (which is generally useful in controlling a wide variety of crawling arthropods). Such well-known toxicants include, but are not limited to, a variety of commercially-available organic compound-based toxicants, including organophosphorus compounds, and carbamates as well as inorganic toxicants and insect growth regulators. (See, for example, "Pesticides: Theory and Application", by George W. Ware, published 1983 by W. H. Freeman and Company.)

For purposes of the present invention, suitable organophosphorus compounds include phosphates, phosphonothionates, and phosphorothionates. For example, suitable, well-known organophosphorus compounds, useful as toxicants in the present invention, include, but are not limited to: acetylphosphoramidothioic acid O,S-dimethyl ester, also known by its so-called "trivial" name of "Acephate", and commercially available under the "Ortho" and "Orthene" brand names (see also U.S. Pat. Nos. 3,716,600 and 3,845,172, both to Chevron); phosphorothioic acid O,O-diethyl O-(3,5,6-trichloro-2-pyridinyl) ester, also known by its trivial name of "Chlorpyrifos", and commercially available under the "Dursban", "Lorsban", and "Pyrinex" brand names (see also U.S. Pat. No. 3,244,586 to Dow); phosphorothioic acid O,O-diethyl O-[6-methyl-2-(1-methylethyl)-4-pyrimidinyl] ester, also known by its trivial name "Dimpylate", and commercially available under the "Basudin", "Diazinon", "Diazol", "Garden Tox", "Sarolex", and "Spectracide" brand names (see also U.S. Pat. No. 2,754,243 to Geigy); phosphorothioic acid O,O-dimethyl O-(3-methyl-4-nitrophenyl) ester, also known by its trivial name "Fenitrothion", and commercially available under the "Accothion", "Cyfen", ∓Cyten", "Folithion", "MEP", "Metathion" and "Sumithion" brand names (see also Belgian Pat. No. 594,669 to Sumitomo as well as Belgian Pat. No. 596,901 to Bayer); phosphorothioic acid O,O-dimethyl O-[3-methyl-4-(methylthio)phenyl] also known by its trivial name "Fenthion", and commercially available under the "Baycid", "Baytex", "Entex", "Lebaycid", "Mercaptophos", "Queletox", "Spotton", "Talodex" and "Tiguvon" brand names (see also German Pat. No. 1,116,656 as well as U.S. Pat. No. 3,042,703, both to Bayer; see also Japanese Pat. No. 15,130, which issued in 1964 to Sumitomo); 4-ethoxy-7-phenyl-3,5-dioxa-6-aza-4-phosphaoct-6-ene-8-nitrile 4sulfide, also known by its trivial name "Phoxim", and commercially available under the "Baythion", "Sebacil" and "Volaton" brand names (see also U.S. Pat. No. 3,591,662 to Bayer); and the O,O-dimethyl analog of O-[2-(diethylamino)-6-methyl-4-pyrimidinyl] phosphorothioic acid O,O-dimethyl ester, also known by its trivial name "Pirimiphos-methyl", and commercially available under the "Actellic", "Blex", and "Silo San" brand names, (See, e.g., entry numbers 25, 2167, 2968, 3910, 3927, 7251 and 7372, respectively, in "The Merck Index", 10th ed., published in 1983 by Merck & Co., Inc.)

For purposes of the present invention, suitable carbamates include, but are not limited to: 2,2-dimethyl-1,3-benzodioxol-4-ol methylcarbamate, also known by its trivial name "Bendiocarb", and commercially available under the "Ficam" brand name (see also U.S. Pat. No. 3,736,338 to Fisons); 1-naphthalenol methylcarbamate, also known by its trivial name "Carbaryl", and commercially available under the "Arylam", "Carylderm", "Dicarbam", "Seffein" and "Sevein" brand names (see also U.S. Pat. No. 2,903,478 to Union Carbide); and 2-(1-methylethoxy)phenol methylcarbamate, also known by its trivial name "Propoxur", and commercially available under the "Baygon", "Bifex", "Blattanex", "Invisi-Gard", "Propyon", "Sendran", "Suncide" and "Unden" brand names (see also U.S. Pat. No. 3,111,539 to Bayer). (See e.g., entry Nos. 1035, 1766 and 7737, respectively, in "The Merck Index", 10th ed.)

For purposes of the present invention, suitable inorganic toxicants include, but are not limited to, certain well known stomach poisons, such as the arsenicals (i.e. any one of a variety of well-known arsenic-containing compounds), certain heavy metal-containing compounds, and certain fluorine-containing compounds, as well as boric acid, silica gel and sodium borate. (See, e.g., page 62 of "Pesticides: Theory and Application" by George W. Ware.)

Insect growth regulators (IGRs), occasionally referred to as "biorationals", are rather specific chemicals which are presently believed to be generally environmentally "safe". Moreover, certain ones of the presently-known IGRs tend to closely resemble certain biological, organic-type chemicals produced by certain insects and/or plants.

IGRs function by altering growth and development of arthropods. The observed effects of IGRs upon metamorphosis, upon reproduction, upon behavior, and upon embryonic, larval and nymphal development have e.g. been reported in the literature. (See, e.g., page 62 of "Pesticides: Theory and Application" by George W. Ware.) A number of IGRs, found to be effective when utilized in very minute quantities, appear to have no undesirable effects on humans and wildlife. (Id.) Furthermore, it is well known that IGRs are typically nonspecific; and as a result, they are known to affect not only the target species of arthropod but also a variety of other arthropods as well. (Id.)

For purposes of my present invention, suitable insect growth regulators (IGRs) include, but are not limited to: N-[[(4-chlorophenyl)amino]carbonyl]-2,6-difluorobenzamide (a known chitin-synthesis inhibitor), also known by its trivial name "Diflubenzuron", and commercially available under the "Difluron" and "Dimilin" brand names; 2,3,14,22,25-pentahydroxycholest-7-en-6-one ($C_{27}H_{44}O_6$) and 2,3,14,20,22,25-hexahydroxycholest-7-en-6-one ($C_{27}H_{44}O_7$), also known by their trivial names "alpha-Ecdysone" and "beta-Ecdysone", respectively, which are well-known insect-molting hormones that are used for the purpose of controlling the pupation of insects; 7-ethyl-9-(3-ethyl-3- methyloxiranyl)-3-methyl-2,6-nonadienoic acid methyl ester ($C_{18}H_{30}O_3$) and cis-10,11-epoxy-3,7,11-trimethyl-trans,trans-2,6-tridecadienoic acid methyl ester ($C_{17}H_{28}O_3$), both generally described by the trivial term "Juvenile Hormone" (JH), each more particularly recognized (by those skilled in the art) by the abbreviations "C-18 JH" and "C-17 JH", respectively; 3,7,11-trimethyl-2,4-dodecadienoic acid 2-propynyl ester, also known by its trivial name "Kinopreen", and commercially available under the "Enstar" brand name (see also U.S. Pat. No. 3,833,635 to Zoecon); and 11-methoxy-3,7,11-trimethyl-2,4-dodecanoic acid 1-methylethyl ester, also known by its trivial name "Methoprene", and commercially available under the "Altosid", "Apex", "Kabat", and "Manta" brand names (see also U.S. Pat. Nos. 3,818,047 and 3,865,874, both to Zoecon). (See, e.g., entry Nos. 3125, 3470, 5111, 5150 and 5859, respectively, in the "The Merck Index", 10th ed.; and pages 62–64 of "Pesticides: Theory and Application" by G. W. Ware.) The term "Juvenile Hormone", as used in this application, includes: the so-called "JH mimic" and "JH analog" (JHA) IGRs, and their broader synonyms, the so-called "juvenoids" and "juvegens". (See, e.g., page 62 of "Pesticides: Theory and Application" by Ware.)

Still further, and in addition to what was specifically identified hereinabove, certain other toxicants, particularly effective in controlling a variety of arthropods (except ants), in general, and suitable for purposes of the present invention include, but are not limited, cypermethrin, other synthetic pyrethroids (such as permethrin, deltamethrin, alphamethrin, and cyphenothrin and the like), and natural pyrethrum. However, as was briefly noted immediately above, pyrethroids (which have been observed as being generally repellent to most ants at even minute concentrations) would of course not be included in the formulations of my composition-of-matter when such is to be used to control ants.

Such toxicants, suitable for purposes of my present invention, may be employed in my arthropodicidally-active composition-of-matter in any desired proportion, generally ranging from about 0.01 to about 2.5 parts-by-weight, and preferably ranging from about 0.1 to about 2.0 parts-by-weight, per one-hundred (100) parts-by-weight of my novel arthropodicidally-active composition-of-matter.

As yet another optional ingredient, the novel arthropodicidally-active composition-of-matter of my present invention can further include a foam stabilizer, an emulsion stabilizer, or both, as desired. Stabilizers of these sorts are well-known to those skilled in the art.

As was briefly mentioned above, one aspect or feature of my present invention is directed to an arthropodicidally-active composition-of-matter which is characterized as a stable foam matrix. More particularly, such a composition-of-matter, as was also briefly mentioned above, includes an emulsifier in the aqueous lower alkanol solvent. The emulsifier is preferably of the so-called "nonionic" charge type. The amount of emulsifier in the solvent is effective for forming the stable foam matrix.

By arthropodicidally-active composition-of-matter can be dispensed from various types of dispensing systems and equipment, e.g., from spray guns, portable aerosol containers, cans and the like, to provide an advantageous way of applying the arthropodicidally-active stable foam matrix of my present invention into variety of void spaces including, but not limited to, cracks and crevices, beneath doors and around windows, and in pipe, drains and other conduit. My stable foam matrix can thus readily be formed-in-place in a variety of void spaces. Furthermore, such a formed-in-place stable foam matrix generally substantially fills certain void spaces, thereby providing a so-called "positive" arthropodicidally-active barrier.

Prior to formation of the above-discussed foam matrix, the arthropodicidally-active composition-of-matter of my present invention is a so-called "water out" emulsion (i.e., an "oil-in-water" emulsion). Suitable emulsifiers for purposes of producing a stable foam matrix in accordance with the principles of my present invention include, but are not limited to, certain ones of the so-called "block polymers", the so-called "ethoxylated alcohols", the so-called "ethoxylated alkyl phenols", the so-called "ethoxylated amines" (and/or "amides"), the so-called "ethoxylated" and "propoxylated" fatty acids, the so-called "ethoxylated fatty esters" (and "oils") as well as the "fatty esters", the so-called "glycerol esters" and "glycol esters" as well as the lecithins (and the lecithin derivatives), the so-called "monoglycerides" (and their derivatives), certain phosphate derivatives as well as certain phosphate esters, the so-called "sorbitan" derivatives, and the so-called "sucrose esters" (and their derivatives). Emulsifiers of these types are commercially available and are well-known tot hose skilled in the art. (See. e.g., pages 287–290 of the 1986 North American Edition of "McCutcheon's Emulsifiers & Detergents", published by the McCutcheon Division of the MC Publishing Co., of Glen Rock, N.J.).

As yet another optional ingredient, my foamable arthropodicidally-active composition-of-matter can include a propellant for causing the emulsifier-containing arthropodicidally-active composition-of-matter (which is characterized as an "oil-in-water" emulsion) to produce the stable arthropodicidally-active foam matrix. Such a stable foam matrix, as was briefly mentioned above, is water-soluble.

When the foamable arthropodicidally-active composition-of-matter further includes the optional propellant ingredient, such a propellant is present in an amount of about 5 to about 20 parts-by-weight, preferably is present in an amount of about 7 to about 12 parts-by-weight, and more preferably is present in an amount of about 8 to about 10 parts-by-weight, based upon one-hundred (100) parts-by-weight of the propellant-containing, foamable, arthropodicidally-active composition-of-matter of my present invention.

Normally, the selected propellant is immiscible with the aqueous phase; but it need not be. In particular, selected water-soluble propellants, such as dimethyl ether (DME), are suitable for purposes of my present invention. Further suitable water-soluble or partially water-soluble propellants include nitrous oxide (which is moderately soluble in water), and carbon dioxide (which is soluble in water in only very minute concentration).

Additional suitable propellants, for purposes of my present invention include, but are not limited to, certain liquefied and compressed gases. Suitable liquefied gases, for purposes of my present invention, include certain hydrocarbon propellants (such as $C_1$ to $C_4$ hydrocarbons) and certain halogenated propellants (such as the various commercially-available halogenated propellants collectively known in the art generally as "Freon"). Illustrative of the preferred hydrocarbon propellants are propane, n-butane, isobutane, and mixtures thereof. Additional suitable compressed gases, for purposes of the present invention, include air and nitrogen.

A presently preferred propellant, often referred to in the art simply as "A-46", has a vapor pressure of about 46 pounds per square inch gauge (psig) and comprises about 80 mole percent isobutane and about 20 mole percent propane. Another presently preferred propellant is "A-31", which is isobutane.

In addition to the several above-identified ingredients, the arthropodicially-active composition-of-matter of my present invention can optionally include a fragrance, a microorganism growth inhibitor (or another, suitable so-called "preservative"), and/or a metal-corrosion inhibitor. One such illustrative microorganism growth inhibitor (or preservative) is formaldehyde. It can well be appreciated by those skilled in the art that inclusion of a preservative and/or a metal-corrosion inhibitor may be desirable, for a variety of reasons. The arthropodicidally-active composition-of-matter of my present invention can further optionally include a disinfectant agent, a dye (or a pigment) to produce a "colored" foam, if desired.

Illustrative of a suitable metal-corrosion inhibitor, for purposes of my present invention, is a compound selected from the group consisting of sodium benzoate, sodium nitrite, and the combination comprising sodium benzoate and sodium nitrite.

My present invention will hereunder be described in even greater detail by reference to the following Examples which are given here for illustrative purposes only and are by no means intended to limit the scope of my present invention.

EXAMPLE 1

Cockroach-Edible Stable Foam Matrix

The following formulation ("Formulation I") was prepared for purposes of testing the efficacy of the arthropodicidally-active composition-of-matter of my present invention.

| Ingredient Name | Formulation I Function | Weight Parts |
|---|---|---|
| water | solvent | 52.25 |
| ethanol | solvent | 15.00 |
| maltose | attractant | 10.00 |
| soybean oil | attractant | 10.00 |
| vanilla extract | attractant | 1.00 |
| "Polawax" | emulsifier | 1.00 |
| "Orthene" | toxicant | 0.50 |
| "Fenoxycarb" | toxicant | 0.25 |
| "A-31" | propellant | 10.00 |

Preparation of Formulation I

The above-presented formulation ("Formulation I") was prepared as follows. The ethanol (solvent) was introduced into a first mixing vessel of suitable volume; and the water (solvent) was introduced into a second mixing vessel, also of suitable volume.

Into the ethanol-containing vessel were added, with mild agitation, the "Fenoxycarb" (toxicant) ingredient (an IGR), as well as the "Polawax" (emulsifier) ingredient and the soybean oil (attractant) ingredient. "Fenoxycarb" is the so-called trivial (or common) name of the insect growth regulator (toxicant) more particularly known as ethyl[2-(para-phenoxyphenoxy)ethyl] carbamate.

The ethanol-containing vessel was then heated in a manner so that the ethanol solvent reached a temperature of 40° C., while maintaining moderate agitation, until the above-identified toxicant, emulsifier and attractant ingredients dissolved therein, thereby producing a heated, ingredient-containing ethanol solution.

Into the water-containing vessel were added, with vigorous agitation, the maltose (attractant) ingredient, the "Orthene" (toxicant) ingredient and the vanilla extract (attractant) ingredient. The water-containing vessel was then heated, while maintaining vigorous agitation, until the above-identified attractant and toxicant ingredients dissolved therein, thereby producing a heated, ingredient-containing aqueous solution.

Next, the heated, ingredient-containing ethanol solution was slowly added to the heated, ingredient-containing aqueous solution, utilizing moderate agitation, thereby producing an oil-in-water (i.e., "water-out") emulsion. The thus-produced water-out emulsion was then heated in a manner so as to maintain a temperature of 40° C. (for the thus-produced emulsion), while maintaining agitation, for thirty (30) minutes.

Thereafter, ninety (90) weight-parts of the thus-produced water-out emulsion were charged, along with ten (10) weight-parts of the "A-31" (propellant) ingredient, into a commercially-available aerosol container of suitable volume. The thus-charged aerosol container was then used in connection with the following efficacy experiments.

Experimental Equipment and Subject Matter

A plastic tray having an area of about 130 inches (about 10 inches by about 13 inches) and a depth of about 4 inches was obtained, for the purpose of performing certain observed, efficacy experiments upon cockroaches. The cockroaches employed were German cockroaches, technically known as *Blattella germanica*.

Experimental Procedures

Into such a tray was placed a pair of spaced-part, untreated "hides." As is well known by those skilled in the art, a so-called "hide" is a generally enclosed structure, having slits or other openings that allow free access, within which "hides" cockroaches prefer to congregate.

Twenty-five (25) male German cockroaches were utilized per replicate.

The 25 cockroaches were introduced onto the tray (containing the hides), and were given a time period of about eighteen (18) hours to acclimate themselves to the tray and hides.

After such an acclimation period, a 2-inch by 2-inch glass slide was obtained. A suitable quantity of the above-discussed formulation (i.e., "Formulation I") was then dispensed, from a distance of about six (6) inches, onto the glass slide, thereby producing a foam matrix of suitable volume on such a slide. The freshly-dispensed foam matrix-supporting glass slide was then immediately placed onto the plastic tray between the hides. After thus placing the foam-containing slide onto the tray, the efficacy of the foam matrix upon the cockroaches was observed.

No food or water was available to the cockroaches during the acclimation or observation periods.

In the following tables ("Table I and Table II"), the reported data represents the average of two (2) replicates.

TABLE I

| Mortality Observations | |
|---|---|
| Average Time to First Feeding | Average Percent Mortality After Two (2) Hours |
| 65 seconds | 100 Percent |

Five-Day Aging Procedure

Next, a second, suitable quantity of the above-discussed formulation (i.e., "Formulation I") was then dispensed, from a distance of about six (6) inches, onto a second 2-inch by 2-inch glass slide; and thereafter, the foam-containing glass slide was maintained at room temperature (i.e., 25° C.) for five (5) days. After such a 5-day period, the second foam matrix-containing glass slide was again placed between two (2) spaced-apart hides, together containing twenty-five (25) male cockroaches which had similarly been given an eighteen (18) hour acclimation period. After thus placing the 5-day-aged foam-containing slide onto the tray, the efficacy of the foam matrix upon the cockroaches was observed. The table II observations also represent the average of two (2) replicates.

TABLE II

| | | | Observed Mortality, Percent Average | | | | |
|---|---|---|---|---|---|---|---|
| After ¾ Hrs. | After 1 Hr. | After 1¼ Hr. | After 1½ Hr. | After 1¾ Hr. | After 2 Hrs. | After 3 Hrs. | After 4 Hrs. |
| 16% | 30% | 42% | 52% | 66% | 74% | 90% | 98% | sifier composite" that is commercially available from Croda Inc. (See page 259 of the 1986 edition of "McCutcheon's Functional Materials", North American Edition, published by The Manufacturing Confectioner Publishing Co. of Glen Rock, N.J. 07452.) "Polawax A-31", the emulsifier utilized in producing Formulation IV, is a so-called "nonionic emulsifying was" that is also commercially available from Croda Inc. (See page 139 of the 1986 edition of "McCutcheon's Emulsifier & Detergents", International Edition, also published by the Manufacturing Confectioner Publishing Co.)

"Polawax" is more particularly characterized as the reaction product of certain fatty alcohols with ethylene oxide. In physical appearance, it is a wax-like non-ionic solid having a pH in 3 weight percent aqueous solution (at 45° C.) of 5.5 to 7.0, a melting point of 48° to 52° C., a hydroxyl value of 178 to 192, an iodine value (Wijs) of 3.5 max., and a saponification value of 14 max.

"Polawax A-31" is a so-called "aerosol grade" of "Polawax" (emulsifier). The physical properties of "Polawax A-31" are identical to the physical properties of "Polawax" except that "Polawax A-31" possesses greater clarity.

EXAMPLE 2

Additional Stable Foam Efficacy Observations

The following formulations ("Formulations II through V") were likewise prepared for purposes of testing the efficacy of my novel arthropodicidally-active composition-of-matter.

| | Formulations II through V | | | | |
|---|---|---|---|---|---|
| Ingredient Name | Ingredient Function | Formulation Weight Parts | | | |
| | | II | III | IV | V |
| water | solvent | 53.00 | 52.00 | 53.00 | 52.00 |
| ethanol | solvent | 15.00 | 15.00 | 15.00 | 15.00 |
| "Corn Sweet 90" | attractant | 10.00 | 10.00 | 10.00 | 10.00 |
| soybean oil | attractant | 10.00 | 10.00 | 10.00 | 10.00 |
| "Polawax" | emulsifier | 1.00 | 2.00 | — | 1.00 |
| "Polawax A-31" | emulsifier | — | — | 1.00 | — |
| vanilla extract | attractant | — | — | — | 1.00 |
| cetyl alcohol | stabilizer | 0.50 | 0.50 | 0.50 | 0.50 |
| "Orthene" | toxicant | 0.50 | 0.50 | 0.50 | 0.50 |
| "A-31" | propellant | 10.00 | 10.00 | 10.00 | 10.00 |

The above-presented formulations, namely Formulation II through Formulation V, were prepared as follows.

In the preparation of each of the above-listed formulations, the ethanol (solvent) was introduced into a first mixing vessel of suitable volume; and the water (solvent) was introduced into a second mixing vessel, also of suitable volume. Into the ethanol-containing vessel were added, with mild agitation, the soybean oil (attractant) ingredient, the above-named emulsifier ingredient, and the above-listed cetyl alcohol stabilizer ingredient. Cetyl alcohol, a so-called "fatty" alcohol which is schematically represented as $C_{16}H_{33}OH$, is believed to function both as an emulsion stabilizer and as a foam stabilizer as well. "Polawax", the emulsifier utilized in producing Formulations II, III and V, is a so-called "emul- The ethanol-containing vessel was then heated in a manner so that the ethanol solvent reached a temperature of 40° C., while maintaining moderate agitation, until the above-identified emulsifier, attractant and stabilizer ingredients dissolved therein, thereby producing a heated, ingredient-containing ethanol solution.

Into the water-containing vessel were added, with vigorous agitation, the "Orthene" (toxicant) ingredient and the "Corn Sweet 90" (attractant) ingredient. "Corn Sweet 90" is the brand name of a commercially available corn sweetener that is compositionally made up of about 90 weight-parts (corn-derived) fructose and 10 weight-parts other corn-derived sweeteners. In the preparation of Formulation V, the vanilla extract (attractant) ingredient was also added into the water-containing vessel. In the preparation of each of the above-listed formulations, the water-containing vessel was then heated, while maintaining vigorous agitation, until the above-identified attractant and toxicant ingredients dissolved therein, thereby producing a heated, ingredient-containing aqueous solution.

In the preparation of each of the above-listed formulations, the heated, ingredient-containing ethanol solution was then slowly added to the heated, ingredient-containing aqueous solution, utilizing moderate agitation, thereby producing an oil-in-water emulsion. The thus-produced oil-in-water emulsion was then heated in a manner so as to maintain a temperature of 40° C. (for each of the thus-produced emulsions of Formulations II through V), while maintaining agitation, for thirty (30) minutes.

Thereafter, and for each of Formulation II through Formulation V, ninety (90) weight-parts of the thus-produced "oil-in-water" emulsion was charged, along with ten (10) weight-parts of the "A-31" (propellant) ingredient, into a commercially-available aerosol container of suitable volume. The thus-charged aerosol container was then used to connection with the following efficiency experiments.

The equipment and procedures discussed above in EXAMPLE 1 were utilized for EXAMPLE 2. Again, twenty-five (25) male German cockroaches were utilized per replicate. In the following table ("Table III"), the reported data represents the average of two (2) replicates.

TABLE III

| | Mortality Observations | | | | | | |
|---|---|---|---|---|---|---|---|
| | Average Percent Mortality | | | | | | |
| Formulations II through V of Example 2 | After ½ Hours | After ¾ Hours | After 1 Hour | After 1¼ Hours | After 1½ Hours | After 1¾ Hours | After 2 Hours |
| Formulation II | 4 | 24 | 54 | 70 | 80 | 98 | 100 |
| Formulation III | 4 | 30 | 54 | 84 | 96 | — | 100 |
| Formulation IV | 6 | 36 | 72 | 86 | 96 | 100 | — |
| Formulation V | 6 | 46 | 74 | 88 | 100 | — | — |

The five-day aging procedure was not repeated in connection with EXAMPLE 2.

What has been described herein is a novel arthropodicidally-active composition-of-matter, and methods for producing the same. While my present invention has been described with reference to certain preferred embodiments, it is to be understood that the scope of my present invention is not to be limited to such preferred embodiments. On the contrary, alternatives, changes and/or modifications will become readily apparent to those skilled in the art upon reading my foregoing description. Accordingly, such alternatives, changes and modifications are to be considered as forming a part of my present invention insofar as such fall within the spirit and scope of the appended claims.

I claim:

1. An arthropodicidally-active composition-of-matter characterized as a formulation, comprising:
   an aqueous lower alkanol solvent consisting essentially of water and about 3 parts-by-weight to about 40 parts-by-weight of a $C_1$ to $C_4$ lower alkanol, based upon 100 parts-by-weight of total water and lower alkanol;
   a toxicant contained within the solvent; and
   an effective amount of an emulsifier, with respect to the amount of solvent and contained within the solvent, for enabling the formulation to form a foam matrix that is able to remain stable for at least about 5 days, the toxicant being present in an amount of about 0.01 parts-by-weight to about 2.5 parts-by-weight, based upon 100 parts-by-weight of the arthropodicidally-active composition-of-matter, the emulsifier being present in an amount of at least about 1 weight percent based upon total weight of the arthropodicidally-active composition-of-matter, wherein the formulation is characterized as a water-out emulsion prior to formation of the foam matrix.

2. The arthropodicidally-active composition-of-matter of claim 1 wherein the formulation additionally contains about 0.5 parts-by-weight to about 20 parts-by-weight of an attractant, based upon 100 parts-by-weight of the arthropodicially-active composition-of-matter.

3. The arthropodicidally-active composition-of-matter of claim 1 wherein the lower alkanol is ethanol.

4. The arthropodicidally-active composition-of-matter of claim 1 further comprising a propellant.

* * * * *

UNITED STATES PATENT AND TRADEMARK OFFICE
CERTIFICATE OF CORRECTION

PATENT NO. : 5,116,618
DATED : May 26, 1992
INVENTOR(S) : John D, Hagarty

It is certified that error appears in the above-indentified patent and that said Letters Patent is hereby corrected as shown below:

Col. 1, line 7, please insert the words -- continuation of -- immediately preceding "Ser. No. 07/339,565".

Col. 1, line 17, please delete "si" and insert the word -- is -- in place thereof.

Col. 1, line 47, please delete "annular" and insert the word -- annually" in place thereof.

Col. 1, line 56, immediately preceding the word "interspersed" please delete "a" and insert the word -- is -- in place thereof.

Col. 1, line 57, please delete "foal" and insert the word -- foam -- in place thereof.

UNITED STATES PATENT AND TRADEMARK OFFICE
CERTIFICATE OF CORRECTION

PATENT NO. : 5,116,618

DATED : May 26, 1992

INVENTOR(S) : John D. Hagarty

It is certified that error appears in the above-indentified patent and that said Letters Patent is hereby corrected as shown below:

Col. 3, line 44, please delete "of" appearing at the very end of the line, substituting the word -- or -- in place thereof.

Col. 4, line 65, please delete "port" appearing at the very end of the line, substituting the word -- pork -- in place thereof.

Col. 8, line 27, at the very end of the line please delete "tot hose", substituting the words -- to those -- in place thereof.

Col. 12, line 7, please change "was" to -- wax -- .

Signed and Sealed this

Third Day of August, 1993

MICHAEL K. KIRK

Attest:

Attesting Officer

Acting Commissioner of Patents and Trademarks